United States Patent [19]

Zulliger-Bopp et al.

[11] Patent Number: 4,784,847

[45] Date of Patent: Nov. 15, 1988

[54] WINE-CONTAINING SKIN-CARE PRODUCTS

[76] Inventors: Monika G. Zulliger-Bopp; Alfred Zulliger, both of Ettingen, Switzerland

[21] Appl. No.: 43,609

[22] Filed: Apr. 28, 1987

[51] Int. Cl.$^4$ .............................................. A61K 35/78
[52] U.S. Cl. ..................................... 424/69; 424/195.1
[58] Field of Search ................................ 424/195.1, 69

[56] References Cited

U.S. PATENT DOCUMENTS

| | | | |
|---|---|---|---|
| 9,252 | 9/1807 | Rullmann | 424/195.1 |
| 45,410 | 12/1864 | Horner | 424/195.1 |
| 126,363 | 4/1872 | Whiteley | 424/195.1 |
| 131,935 | 10/1872 | Bent | 424/195.1 |
| 136,308 | 2/1873 | Curtis | 424/195.1 |
| 367,406 | 8/1887 | Jones | 424/195.1 |
| 395,824 | 1/1889 | Gentry | 424/195.1 |
| 406,071 | 7/1889 | Vogt | 424/195.1 |
| 408,488 | 8/1889 | Larochelle | 424/195.1 |
| 4,382,961 | 5/1983 | Gardy et al. | 424/195.1 |
| 4,460,488 | 7/1984 | Grollier et al. | 424/195.1 X |
| 4,569,839 | 2/1986 | Grollier et al. | 424/195.1 X |
| 4,581,230 | 4/1986 | Grollier et al. | 424/195.1 X |
| 4,702,915 | 10/1987 | Keri et al. | 424/195.1 |

FOREIGN PATENT DOCUMENTS 1098166  7/1961  Fed. Rep. of Germany .
1078286  8/1961  Fed. Rep. of Germany .

Primary Examiner—Nancy A. B. Swisher
Attorney, Agent, or Firm—Shlesinger Arkwright & Garvey

[57] ABSTRACT

A wine-containing skin-care cream including a watery phase comprising by weight of the cream of about 40% to about 83% of alcohol extracted wine and about 0.5% to about 5% of Sorbitol as a stabilizer for the wind combined with about 60% to about 17% of an oily phase comprising one or more ingredients including vegetable oils, mineral oils and emulsifiers.

10 Claims, No Drawings

WINE-CONTAINING SKIN-CARE PRODUCTS

FIELD OF THE INVENTION

The present invention relates to skin-care products containing wine, and more particularly to skin-care products containing wine in combination with an extract derived from the leaves of grape plants in order to enhance skin toning properties as well as to regulate superficial blood circulation and to otherwise produce beneficial effects upon the skin due to the biological action of the naturally occurring ingredients found in wine and extracts thereof.

BACKGROUND OF THE INVENTION

The use of wine in skin-care products is disclosed in German Patentschrift No. 1,078,286, published Aug. 3, 1961, as well as in corresponding French patent No. 1,160,592, published July 18, 1958, and in Swiss patent No. 352,096, published Mar. 30, 1961. In addition, German Patentschrift No. 1,098,166, published July 20, 1961, discloses dental-care products containing wine.

In German Patentschrift No. 1,078,286, a skin cream is disclosed which is comprised of 45 parts of bees wax, 50 parts of spermaceti, 30 parts of lanolin, 30 parts of sesame oil and 200 parts of Mosel wine. Also disclosed is a face lotion containing Mosel wine and brandy. The specification discloses that the above-mentioned wine-containing body care substances increase the motor activity of the skin, i.e., the treated skin parts have higher blood flow due to the dilation of the superficial blood vessel.

In addition, other beneficial effects upon the skin result from the biological action of the naturally occurring ingredients present in the wine, either individually or in combination with each other. Included among these ingredients are various acids, nitrogen compounds, carbohydrates, minerals, pigments, oils and vitamins.

It has been found that some skin types are adversely affected by the aforementioned wine-containing skin-care products in large part due to the high alcohol content present therein. Alcohol has been shown to dehumidify, that is, remove moisture from the skin leading to increased drying of the skin.

It would therefore be advantageous to produce wine-containing skin-care products in which the quantity of alcohol is greatly reduced in order to avoid dehumidification of the skin, while at the same time deriving the benefits of the naturally occurring ingredients present in the wine.

SUMMARY AND OBJECTS OF THE INVENTION

The present invention avoids the disadvantages associated with the prior art compositions by providing skin-care products containing wine in which a large percentage of the alcohol is initially eliminated by an extraction process, thereby concentrating the remaining beneficial ingredients. Preferably, the treated wine is combined with a powder extract derived from the leaves of grape plants in order to obtain additional skin enhancing properties due to the naturally occurring ingredients associated therewith. The concentrated wine and extract powder are mixed with various other stabilizing ingredients and carriers to produce moisturizing creams, nourishing creams and body lotions of the desired consistency.

It is therefore an object of the present invention to provide improved wine-containing skin-care products having reduced alcohol content.

Another object of the present invention is to provide wine-containing skin-care products which additionally contain extracts derived from the leaves of grape plants.

A further object of the present invention is to provide wine-containing skin-care products which have excellent toning properties, which act as natural astringents and which regulate superficial blood circulation.

Still a further object of the present invention is to provide wine-containing skin-care products which greatly enhance skin tonus and turgor.

The foregoing as well as other objects and advantages of the present invention will become apparent from the following detailed description.

DETAILED DESCRIPTION OF THE INVENTION

In preparing wine-containing skin-care products according to the present invention, red or pink wines as well as white wines may be used depending upon the properties required of the composition. In general, white and pink wines contain a greater percentage of acids than red wines, while red wines have a higher tannin content.

The wine is first concentrated by extracting most of the alcohol along with some of the water to reduce the original volume by about 10 to about 15%. The extraction process is performed at a temperature of about 70° C. under vacuum.

Next, the concentrated wine is mixed with a powder extract of grape plant leaves and a quantity of Sorbitol USP as a stabilizer at room temperature and subsequently heated to about 70° C. The powder extract is derived from ground leaves of the grape plant which are extracted at relatively low temperature so as not to deleteriously affect the natural properties of the oils, enzymes etc., extracted from the plant. Extraction may be achieved by various methods, for example, using a mixture of water and propyleneglycol or using alcohol or vapor. The extract is then reduced to a powder form by evaporation, preferably by freeze drying.

The powder extract contains derivatives of polyphenols and anthocianics as well as tannin, flavinoids and vitamins such as C and P. The extract has excellent toning properties, acts as a natural astringent and regulates superficial blood circulation. Furthermore, the powder extract intensifies the natural beneficial properties of the wine, without introducing additional alcohol into the skin-care compositions. From about 0.4% to about 3% by weight of powder extract may be used. Less is of no benefit and more makes the composition too harsh. About 0.4% to about 1% is generally preferred.

The remaining ingredients of the composition, namely, vegetable oils, mineral oils, emulsifiers etc. comprise the oily phase. Among the compounds which may be present in the oily phase are mineral oil, ozokerite, glycerin oleate, lanolin alcohol, vegetable oil, lanolin, bees wax, glycerin, isopropyl lanolate, cholesterine, sorbitane sesanioleate, aluminum stearate, propylparaben, cetearyl alcohol, petrolatum, castor oil, sodium cetearyl sulfate, isopropylmyristate, hydroxylated lanolin, glyceryl stearate, decyl oleate, silicon oil as well as anti-oxidation agents and perfumes.

The oily phase is heated to about 85° C. and mixed with the liquid phase (concentrate wine, extract powder and Sorbitol), for example, in a vacuum mixer. The mixture is then homogenized and finally cooled. Alternatively, the mixture may be homogenized in the vacuum mixer.

The amount of wine present in the various compositions can vary from about 40% by weight to about 83% by weight. The amount of vegetable oils, mineral oils and emulsifiers used are dependent upon the quantity of wine used so as to provide the balance of the composition. Generally, the combined vegetable oils, mineral oils and emulsifiers account for about 60% by weight to about 17% by weight of the composition.

The skin creams of the present invention are smoother than the products disclosed in the aforementioned prior art due to improvements resulting from the use of more recently developed raw materials including improved emollients and stabilizers.

Instead of using the wines previously mentioned, an alternative composition may be prepared with champagne.

EXAMPLE 1

| INGREDIENTS | % BY WEIGHT |
|---|---|
| Mixture of: Red wine (alcohol extracted), Sorbitol and powder extract of grape plant leaves* | 50.5 |
| Mixture of: Mineral oil, ozokerite, glycerin oleate and lanolin alcohol | 15 |
| Vegetable oil | 6.25 |
| Lanolin | 8 |
| Mixture of: Mineral oil and lanolin alcohol | 7 |
| Bees wax | 2.7 |
| Glycerin | 7.5 |
| Isopropyl lanolate | 1 |
| Cholesterine | 1 |
| Mixture of: Sorbitan sesanioleate, bees wax and aluminum stearate | .75 |
| Propylparaben } Antioxidizing agent } Perfume | .3 |
| | 100 |

*Mixture comprised of 95.6 parts of red wine (alcohol extracted), 3.6 parts of sorbitol and .8 parts of powder extract.

EXAMPLE 2

| INGREDIENTS | % BY WEIGHT |
|---|---|
| Mixture of: White wine (alcohol extracted) and Sorbitol** | 82.5 |
| Mixture of: Cetearyl alcohol, lanolin, vegetable oil, mineral oil and petrolatum | 4 |
| Mixture of: Cetearyl alcohol, castor oil and sodium cetearyl sulfate | 3.2 |
| Paraffin | 4 |
| Isopropylmyristate | 2 |
| Hydroxylated lanolin | 1 |
| Mixture of: Mineral oil and lanolin alcohol | 1 |
| Glyceryl stearate | .7 |
| Glycerin | .5 |
| Decyl oleate | .3 |
| Silicon oil | .1 |
| Propylparaben } Antioxidizing agent } Perfume | .7 |
| | 100 |

**Mixture comprised of 98 parts of white wine (alcohol extracted) and 2 parts of sorbitol.

EXAMPLE 3

Same composition as in Example 2 except an equivalent amount of champagne is substituted in place of the white wine.

EXAMPLE 4

Same compositions as in Examples 1, 2 and 3, but the amount of wine is decreased by about 20% to about 30% by weight and replaced by about 20% to about 30% by weight of pasteurized grape juice. The grape juice may be red or white grape juice from red or white grapes.

The grape juice contains a number of additional vitamins etc. which are unavailable in wine or champagne due to fermentation which destroys them.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention and the limits of the appended claims.

What is claimed is:

1. A wine-containing skin-care cream including:
   (a) a watery phase comprising by weight of the cream of about 40% to about 83% of alcohol extracted wine, about 0.4% to about 3% by weight of the cream of a powder extract of grape plant leaves and about 0.5% to about 5% of Sorbitol as a stabilizer for said wine, and
   (b) about 60% to about 17% by weight of the cream of an oily phase comprising an ingredient selected from the group comprising vegetable oil, mineral oil, emulsifier as well as suitable mixtures thereof.

2. A wine-containing skin-care cream as in claim 1, wherein:
   (a) said wine is champagne.

3. A wine-containing skin-care cream as in claim 1, wherein:
   (a) said oily phase additionally includes a minor amount of an oxidizing agent and a perfume.

4. A wine-containing skin-care cream as in claim 1, wherein:
   (a) said watery phase comprising by weight of the cream of about 48.3% of alcohol extracted red wine, about 1.8% of Sorbitol and about 0.4% of powder extract of grape plant leaves, and
   (b) said oily phase comprising by weight of the cream of about 6.25% of vegetable oil, about 8% of lanolin, about 7% of a mixture of mineral oil and lanolin alcohol, about 15% of a mixture of mineral oil, ozokerite, glycerin oleate and lanolin alcohol, about 2.7% of bees wax, about 7.5% of glycerin, about 1% of isopropyl lanolate, about 1% of cholesterine, about 0.75% of a mixture of Sorbitan sesanioleate, bees wax and aluminum stearate and about 0.3% combined weight of propylparaben, an antioxidizing agent and perfume.

5. A wine-containing skin-care cream as in claim 1, wherein:
(a) about 20% to about 30% by weight of said wine is replaced with about 20% to about 30% by weight of pasteurized grape juice.

6. A method of preparing a wine-containing skin-care cream comprising the steps of:
(a) concentrating wine by extracting the alcohol thereby reducing the original volume by about 10% to about 15%,
(b) preparing an extract of ground grape plant leaves by extracting at a temperature of about 70° C. and reducing the extract to a powder form and subsequently combining at room temperature about 40 parts to about 83 parts by weight of said concentrated wine, about 0.4 parts to about 3 parts of said powder extract and about 0.5 parts to about 5 parts by weight of Sorbitol forming a stabilized watery phase and heating said watery phase to about 70° C.,
(c) preparing about 60 parts to about 17 parts by weight of an oily phase comprising an ingredient selected from the group comprising vegetable oil, mineral oil, emulsifier including suitable mixtures thereof,
(d) heating said oily phase to about 85° C. and mixing said oily phase with said heated water phase,
(e) homogenizing the mixture of said oily phase and said watery phase forming a cream, and
(f) cooling said cream.

7. A method as in claim 6, including:
(a) extracting said alcohol at a temperature of about 70° C. under vacuum.

8. A method as in claim 6, including:
(a) reducing said extract to a powder form by freeze drying.

9. A method as in claim 6, wherein:
(a) said wine is selected from the group consisting of red wine, white wine and champagne.

10. A method as in claim 6, wherein:
(a) reducing the amount of concentrated wine by about 20% to about 30% by weight and replacing without 20% to about 30% by weight of pasteurized grape juice.

* * * * *